United States Patent
Fischer et al.

(10) Patent No.: US 10,919,893 B2
(45) Date of Patent: *Feb. 16, 2021

(54) PROCESS FOR THE PREPARATION OF CRYSTALLINE FORM C OF AVIBACTAM SODIUM

(71) Applicant: Sandoz AG, Basel (CH)

(72) Inventors: Michael Fischer, Kundl (AT); Veronika Werner, Kundl/Tirol (AT); Andreas Lechner, Kundl (AT); Brigitte Staggl, Kundl (AT)

(73) Assignee: Sandoz AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/483,477

(22) PCT Filed: Feb. 7, 2018

(86) PCT No.: PCT/EP2018/053052
§ 371 (c)(1),
(2) Date: Aug. 5, 2019

(87) PCT Pub. No.: WO2018/146134
PCT Pub. Date: Aug. 16, 2018

(65) Prior Publication Data
US 2019/0359612 A1    Nov. 28, 2019

(30) Foreign Application Priority Data
Feb. 8, 2017    (EP) .................................. 17155178

(51) Int. Cl.
*C07D 471/08*    (2006.01)

(52) U.S. Cl.
CPC ........ *C07D 471/08* (2013.01); *C07B 2200/13* (2013.01)

(58) Field of Classification Search
CPC .................................................. C07D 471/08
See application file for complete search history.

(56) References Cited

U.S. PATENT DOCUMENTS 10,265,326 B2 * 4/2019 Hotter ..................... A61P 31/04
2012/0323010 A1   12/2012 Ronsheim et al.

FOREIGN PATENT DOCUMENTS

| WO | 2011042560 A1 | 4/2011 |
| WO | 2014135930 A1 | 9/2014 |
| WO | 2017025526 A1 | 2/2017 |
| WO | 2018037124 A1 | 3/2018 |

OTHER PUBLICATIONS

International Search Report and Written Opinion for PCT/EP2018/053052, dated Aug. 16, 2018, 9 pages.
Pecharsky, Vitalij K., et. al, Fundamentals of Powder Diffraction and Structural Characterization of Materials, Kluwer Academic Publishers, 2003, p. 3.

* cited by examiner

*Primary Examiner* — D Margaret M Seaman
(74) *Attorney, Agent, or Firm* — Luedeka Neely Group, P.C.

(57) ABSTRACT

The invention relates to a process for the preparation of avibactam sodium in polymorphic form C comprising the steps (i) providing a mixture comprising avibactam or a salt thereof and a solvent, wherein the mixture has a water content of less than 2% by weight based on the weight of the mixture; (ii) increasing the temperature of the mixture provided in (i) to at least 55° C. and providing a positive pressure; adding a sodium source to the mixture in step (i) and/or (ii) if the form of avibactam provided in (i) is not avibactam sodium; thereby obtaining avibactam sodium in polymorphic form C.

15 Claims, No Drawings

PROCESS FOR THE PREPARATION OF CRYSTALLINE FORM C OF AVIBACTAM SODIUM

This application is a Section 371 national phase entry of PCT application PCT/EP2018/053052, filed Feb. 7, 2018. This application also claims the benefit of the earlier filing date of European patent application 17155178.1, filed Feb. 8, 2017.

FIELD OF THE INVENTION

The present invention relates to a process for the preparation of crystalline form C of avibactam sodium. The invention also concerns crystalline form C of avibactam sodium prepared by such process as well as a pharmaceutical composition comprising same in combination with one or more antibacterial agents, wherein at least one antibacterial agent is a beta-lactam antibiotic.

BACKGROUND OF THE INVENTION

Avibactam of formula (I) with IUPAC name [(2S,5R)-2-carbamoyl-7-oxo-1,6-diazabicylco[3.2.1]octan-6-yl] hydrogen sulfate is a non-beta-lactam beta-lactamase inhibitor which is reported to have in itself no antibacterial activity at clinically relevant doses.

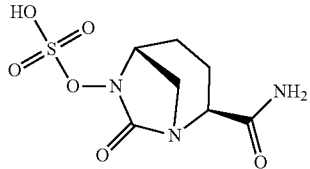

Formula (I)

However, avibactam protects beta-lactam antibiotics from degradation by beta lactamase enzymes and therefore maintains the antibacterial activity of beta-lactam antibiotics. It is therefore useful in conjunction with beta-lactam antibiotics for the treatment of bacterial infections.

WO 2011/042560 A1 refers to crystalline forms of avibactam sodium. For example, WO 2011/042560 A1 discloses anhydrous forms B and D as well as hydrated forms A and E. In addition, according to the application (page 3, lines 6 to 7) a fifth form designated "form C" has been observed but only as a mixture with form A. Specifically, WO 2011/042560 A1 explicitly states that "Form C is not isolated as a pure form but is obtained in a mixture with one or more other forms, in particular Form A" (page 12, lines 5-7). However, the application does not provide any teaching as to how to prepare any such mixture or as to how to obtain said form C.

Further, WO 2014/135930 A1 discloses a crystalline form of avibactam sodium characterized by powder X-ray diffraction. According to the peak list provided on page 6 and the corresponding powder X-ray diffractogram displayed in FIG. 1 of said application this solid can be assigned to a mixture comprising at least form B and form D as described in WO 2011/042560 A1, while form C is not present.

PCT/EP2016/068925 relates to crystalline form C of avibactam sodium, especially in polymorphically pure or essentially polymorphically pure form as well as to an industrially applicable, reliable and robust process for its preparation and to pharmaceutical compositions thereof. This document represents the first disclosure for the reliable preparation and isolation of polymorphically pure form C of Avibactam sodium. Anhydrous form C is polymorphically stable, i.e. it does not convert to other crystalline forms, both under ambient conditions as well as under conditions occurring in the manufacturing of pharmaceutical compositions such as solid pharmaceutical dosage forms. In addition, crystalline form C is physically stable against moisture and highly stable against temperature stress.

In addition, EP16185913.7 relates to avibactam in form of its free acid and a method of producing same. Avibactam free acid is highly useful for pharmaceutical purposes, e.g. due to its low hygroscopicity and stability against moisture and temperature stress. This document further establishes that avibactam free acid and the method of producing same are useful for purification of avibactam.

It is well-known by the skilled person that upon temperature stress or under acidic or basic conditions hydrated forms often tend to hydrolyze. Hydrates are also prone to dehydration, for example, they readily release the bound water when subjected to dry conditions and/or increased temperatures. For example, WO 2011/042560 A1 mentions that the avibactam sodium dihydrate form E tends to lose water and to hydrolyze during long storage and at higher temperature (page 17, lines 1 to 2). It is further stated in the application that form E is particularly stable above a relative humidity of about 70% (page 15, line 25), indicating that this hydrated form is only stable in the presence of moisture. In addition, it was found that form E dehydrates to the monohydrate form A at temperatures above about 60° C. and that form A upon further temperature stress dehydrates to the anhydrous form B. Such conversions of physical forms are critical as pharmaceutical processing and milling usually involves the evolution of heat. Hence, for pharmaceutical purposes anhydrous forms of avibactam sodium are preferred over hydrates.

Besides proper physical properties, the manufacturability of a solid form determines whether it is a feasible candidate for the preparation of a drug product. According to WO 2011/042560 A1 (page 16, lines 30 to 31) anhydrous form D was only obtained as very small crystals, making filtration difficult and slow and hence making it difficult to prepare form D. Thus, due to its limitations with regard to isolation, form D cannot be produced on an industrial scale. In addition, the robustness and reliability of a manufacturing process is a key criterion for physical form selection. WO 2011/042560 A1 (page 17, lines 8 to 14) for example mentions that anhydrous form B is difficult to prepare in the absence of seed crystals and only obtained in a very narrow range of water activity. The seed crystal preparation disclosed in the application (page 16, lines 22 to 26) seems not to be straightforward, let alone industrially applicable. Therefore, a reliable industrial production of anhydrous form B seems to be very challenging.

Since anhydrous forms of Avibactam sodium are preferred for pharmaceutical purposes, anhydrous form C, which does not convert to any other physical form of Avibactam sodium during formulation and storage of a pharmaceutical composition and which is physically stable against moisture and highly stable against temperature stress, is particularly qualified for the preparation of pharmaceutical products.

In view of the above, there is a need for an efficient process which can provide polymorphically pure crystalline form C of Avibactam sodium. One objective of the present invention is therefore the provision of an improved process for the preparation of crystalline form C of avibactam sodium, in particular a process which can be employed on an industrial scale in an efficient manner, i.e. which is cost-effective and does not involve the use of large quantities of organic solvents and/or hazardous reagents.

A further objective of the present invention is the provision of an improved process for the preparation of crystalline form C of avibactam sodium which shows a high tolerance with regard to the starting material employed, i.e. a process which allows for the use of different starting materials such as different crystalline forms and that consistently and reliably provides crystalline form C of Avibactam sodium.

SUMMARY OF THE INVENTION

It was surprisingly found that the process provided by the present invention fulfills all the above-mentioned requirements and represents an industrially-applicable method with which crystalline form C of avibactam sodium can be prepared in an efficient and cost-effective manner.

In particular, the process provided by the present invention allows for the use of different starting materials including the free acid of avibactam and various salts thereof, e.g. its tetrabutylammonium or sodium salt.

Furthermore, the process of the present invention can be employed to obtain crystalline form C of avibactam sodium, which is polymorphically pure or essentially polymorphically pure.

Hence, the present invention relates to a process for the preparation of avibactam sodium in polymorphic form C having a powder X-ray diffractogram comprising reflections at 2-Theta angles of $(6.5\pm0.2)°$, $(14.4\pm0.2)°$, $(15.5\pm0.2)°$, $(18.0\pm0.2)°$ and $(19.3\pm0.2)°$, when measured at a temperature in the range of from 20 to 30° C. with Cu-Kalpha$_{1,2}$ radiation having a wavelength of 0.15419 nm, comprising (i) providing a mixture comprising avibactam or a salt thereof and a solvent, wherein the mixture has a water content of less than 2% by weight based on the weight of the mixture, (ii) increasing the temperature of the mixture provided in (i) to at least 55° C. and providing a positive pressure, adding a sodium source to the mixture in step (i) and/or (ii) if the form of avibactam provided in (i) is not avibactam sodium, thereby obtaining avibactam sodium in polymorphic form C.

DETAILED DESCRIPTION OF THE INVENTION

Different aspects of the invention are described below in further detail by embodiments, without being limited thereto. Each aspect of the invention may be described by one embodiment or by combining two or more embodiments.

The present invention relates to a process for the preparation of avibactam sodium in polymorphic form C having a powder X-ray diffractogram comprising reflections at 2-Theta angles of $(6.5\pm0.2)°$, $(14.4\pm0.2)°$, $(15.5\pm0.2)°$, $(18.0\pm0.2)°$ and $(19.3\pm0.2)°$, when measured at a temperature in the range of from 20 to 30° C. with Cu-Kalpha$_{1,2}$ radiation having a wavelength of 0.15419 nm, comprising (i) providing a mixture comprising avibactam or a salt thereof and a solvent, wherein the mixture has a water content of less than 2% by weight based on the weight of the mixture, (ii) increasing the temperature of the mixture provided in (i) to at least 55° C. and providing a positive pressure, adding a sodium source to the mixture in step (i) and/or (ii) if the form of avibactam provided in (i) is not avibactam sodium, thereby obtaining avibactam sodium in polymorphic form C.

At least step (ii) of this process is carried out in a closed system, e.g. in a sealable vessel having a defined reaction volume. In a preferred embodiment step (ii) is conducted in a sealed reaction vessel. As used herein, the term "sealed reaction vessel" refers to any vessel suitable for carrying out the sequence of steps of the present invention. Specifically, the sealed reaction vessel allows one to tightly control the reaction conditions, in particular temperature and pressure during step (ii). Nevertheless, the sealed reaction vessel may comprise additional inlets and/or outlets for adding or removing material in a controlled manner, e.g. by adding an inert gas in step (ii) in order to obtain the desired positive pressure and/or by adding a sodium source, if necessary. The reaction vessel may also be sealed with a septum which can be punctured to add or remove material.

It is essential that the mixture provided in (i) has a water content of less than 2% by weight, based on the weight of the mixture, when increasing the temperature of the mixture in (ii) to at least 55° C. and providing a positive pressure. Preferably, the mixture provided in (i) has a water content of less than 1.8% by weight, more preferably less than 1.6% by weight, more preferably less than 1.5% by weight, more preferably less than 1.4% by weight, more preferably less than 1.3% by weight, more preferably less than 1.2% by weight, more preferably less than 1.1% by weight, more preferably less than 1.0% by weight, more preferably less than 0.9% by weight, more preferably less than 0.8% by weight, more preferably less than 0.7% by weight, more preferably less than 0.6% by weight, more preferably less than 0.55% by weight based on the weight of the mixture. In various embodiments the mixture provided in (i) may have a water content in a range of from 0.01% by weight to less than 2.0% by weight, preferably of from 0.1% by weight to 1.5% by weight, more preferably of from 0.2% by weight to 0.9% by weight, still more preferably of from 0.3% by weight to 0.6% by weight based on the weight of the mixture. Typically, the mixture is provided by mixing a solid form of avibactam or a salt thereof and a solvent. Thus, the water content of the mixture is usually provided by choosing a solvent having a corresponding water content.

It is also essential that in step (ii) a positive pressure is provided in the mixture provided in step (i). As used herein, "providing a positive pressure" relates to increasing the pressure in step (ii) by any suitable means in the art relative to the pressure at which the mixture in step (i) is provided. There are several ways to provide said positive pressure, which may be used alone or in combination. For example, the positive pressure can be provided by the vapor pressure of the solvent as a result of increasing the temperature of the mixture provided in step (i), e.g. when the temperature is increased above the boiling point of the solvent. The positive pressure can also be provided by pressurization using an inert gas. Also the addition of a sodium source, if necessary, to a sealed reaction vessel may contribute to the positive pressure. The positive pressure can also be provided by a combination of the previously mentioned methods.

Thus, in a preferred embodiment, an inert gas is added in step (ii). Preferably, the inert gas is added to the reaction volume, e.g. to the sealed reaction vessel. In a more preferred embodiment, the inert gas is in a sufficient amount to provide a positive pressure in step (ii), e.g. in the sealed reaction vessel. As detailed above, this may be achieved via an additional inlet of the sealed reaction vessel. Any suitable inert gas can be used, e.g. an inert gas selected from the group consisting of nitrogen and noble gases.

In general, the mixture may be provided in step (i) at any pressure, e.g. at a pressure in the range of from 0.1 bar to 5 bar. In one embodiment the pressure at which the mixture in step (i) is provided may be standard atmospheric pressure of about 1.00 bar. However, in other embodiments the pressure may be lower or higher, e.g. about 0.70, 0.80, 0.90, 0.95, 1.00, 1.05, 1.10, 1.20 or 1.30 bar. As regards said positive pressure provided in step (ii), it is positive, i.e. higher, in relation to the pressure at which the mixture in step (i) is provided.

In a preferred embodiment the positive pressure in (ii) is a positive pressure of at least 5 mbar, preferably at least 8 mbar, more preferably at least 10 mbar, still more preferably at least 15 mbar, still more preferably at least 20 mbar. The positive pressure in (ii) may also be a positive pressure of at least 50 mbar, 60 mbar, 70 mbar, 80 mbar, 90 mbar, 100 mbar, 200 mbar, 300 mbar, 400 mbar or 500 mbar.

In certain embodiments the absolute pressure in (ii) is not more than 210 bar, preferably not more than 12 bar, more preferably not more than 8 bar, still more preferably not more than 5 bar. For example, when the pressure at which the mixture in step (i) is provided is about 1.013 bar or is in the range of from 0.95 bar to 1.05 bar, the absolute pressure in step (ii) may be about 1.1 bar, 1.5 bar, 2.0 bar, 5 bar, 7.0 bar, 11.0 bar.

As will be clear from the explanations hereinbefore, the term "positive pressure" or overpressure does not refer to pressure differences between the reaction mixture and the environment of the system but refers to a pressure difference in the reaction mixture between step (i) and step (ii), namely wherein the pressure in step (ii) is increased relative to step (i). In other words, the absolute pressure in the mixture is increased in step (ii) relative to step (i). For explanatory purposes, if the absolute pressure in the mixture in step (i) is, e.g., 1.00 bar, providing a positive pressure or overpressure in step (ii) will lead to an absolute pressure in the mixture in step (ii) of any value above 1.00 bar, e.g., 1.005 bar, 1.1 bar, or 2 bar. While said pressure increase can be achieved by pressurization using an inert gas, it can also be achieved by any other suitable means or any combination thereof. For example, said pressure increase can be achieved by increasing the temperature of the mixture in a sealed reaction vessel in step (ii) relative to step (i). This is illustrated in, e.g., example 2. When said pressure increase is achieved by other means than pressurization, e.g. by increasing the temperature of the mixture in a sealed reaction vessel in step (ii) relative to step (i), pressurization using an inert gas is optional.

In various embodiments, in step (ii) the pressure in the mixture is increased relative to the pressure in step (i) by at least 5 mbar, preferably at least 8 mbar, more preferably at least 10 mbar, still more preferably at least 15 mbar, still more preferably at least 20 mbar. In other embodiments, the pressure may also be increased by at least 50 mbar, 60 mbar, 70 mbar, 80 mbar, 90 mbar, 100 mbar, 200 mbar, 300 mbar, 400 mbar or 500 mbar.

In a preferred embodiment the solvent is selected from the group consisting of alcohols, esters, ethers, ketones, carbonates, each having an alkyl chain of at least 4 carbon atoms, and mixtures thereof. All of these compounds can be linear, branched or cyclic. E.g., primary, secondary or tertiary alcohols can be used. As stated hereinabove, the solvent typically has a water content of less than 2% by weight, or lower, in order to obtain in the mixture a water content as specified hereinabove.

In a more preferred embodiment the solvent has 4-10 carbon atoms, preferably 4-8 carbon atoms, more preferably 4-6 carbon atoms In an even more preferred embodiment the solvent is selected from the group consisting of a $C_4$-$C_6$ alcohol, a $C_4$-$C_6$ ester, a $C_4$-$C_6$ cyclic ether, a linear or cyclic ketone, a carbonate, and mixtures thereof.

In an especially preferred embodiment the solvent is selected from the group consisting of isobutanol, n-butanol, 2-butanol, 2-methyl-2-butanol, 1,4-dioxane, THF, methyl-THF, ethyl acetate, isobutyl acetate, cyclohexanone, methyl ethyl ketone, methyl isobutyl ketone, diethyl carbonate, and mixtures thereof.

In another especially preferred embodiment the solvent is selected from the group consisting of isobutanol, n-butanol, 2-butanol, 2-methyl-2-butanol, 1,4-dioxane, methyl isobutyl ketone, and ethyl acetate.

It is essential that in step (ii) the temperature of the mixture provided in step (i) is increased to at least 55° C. As regards providing of the mixture in step (i), this may be conducted at any temperature below 55° C., preferably at about room temperature. When increasing the temperature in step (ii), it is preferred to continuously increase the temperature, i.e. to avoid any relative decrease in temperature during the process of increasing the temperature to at least 55° C.

Preferably, in (ii) the temperature is increased to at least 59° C., more preferably to at least 63° C., still more preferably to at least 66° C., still more preferably to at least 70° C., most preferably to at least 73° C. The temperature may also be increased to temperatures of about 75° C., 90° C., 110° C., 120° C. or 126° C. However, it is strongly preferred that the temperature in (ii) is below the decomposition temperature of the solvent.

In various embodiments, in (ii) the temperature is increased to a temperature in the range of from 55° C. to 180° C., preferably of from 59° C. to 150° C., more preferably of from 63° C. to 140° C., still more preferably of from 66° C. to 135° C., still more preferably of from 70° C. to 130° C., most preferably of from 73° C. to 126° C.

In a specific embodiment the temperature is increased in (ii) to at least 66° C. and the positive pressure is a positive pressure of at least 5 mbar. In another specific embodiment the temperature is increased in (ii) to at least 70° C. and the positive pressure is a positive pressure of at least 5 mbar.

In general, the increased temperature and/or positive pressure may be maintained for any suitable amount of time. Preferably, the increased temperature and positive pressure is maintained until formation of form C of avibactam sodium is complete. The exact amount of time depends on the temperature and pressure conditions and/or on the concentration of the starting material in the mixture. In specific embodiments, the increased temperature and positive pressure in (ii) is maintained for at least 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, or 20 minutes. While the increased temperature and positive pressure may be maintained for several hours or even up do 24 h or more, it is preferred that the increased temperature and positive pressure in (ii) is maintained for not more than 180 min, preferably not more than 120 min, more preferably not more than 60 min, still more preferably not more than 50 min, still more preferably not more than 45 min, most preferably not more than 40 min. For economic reasons, it will be advisable to maintain the increased temperature and positive pressure for a minimum amount of time.

In specific embodiments, the increased temperature and positive pressure in (ii) is maintained for 2-50 min, preferably 5-45 min, more preferably 10-40 min, still more preferably 15-40 min, most preferably 20-40 min.

As regards the avibactam starting material, the process of the present invention provides high flexibility. On the one hand, it is possible to use avibactam in the form of its free acid. On the other hand, avibactam may be used in the form of a salt, e.g. avibactam sodium or a non-sodium salt such as avibactam tetrabutylammonium. While the general concept of the present invention is applicable to all forms of avibactam, it is apparent that in case a non-sodium form of avibactam is used, it is necessary to add a suitable sodium source to the mixture.

Avibactam or the salt thereof may be provided in step (i) in any suitable physical form, e.g. in crystalline form, amorphous form or a mixture thereof. In a preferred embodiment avibactam or a salt thereof is provided in crystalline form.

In one aspect of the present invention the mixture provided in (i) is a mixture comprising a solvent and avibactam sodium, preferably in crystalline form. Avibactam being already present in the form of its sodium salt, it is not necessary to add a sodium source in this aspect. For example, polymorphic forms of avibactam sodium as disclosed in WO 2011/042560 A1 can be used. Thus, the form of avibactam provided in a mixture in (i) may be any of crystalline forms "A", "B", "D" or "E" of avibactam sodium or a combination thereof. For example, the mixture provided in (i) may be a suspension of crystalline avibactam sodium in the solvent. In a preferred embodiment of this aspect, step (i) is providing a suspension comprising crystalline form "A" of avibactam and a solvent, wherein the mixture has a water content of less than 0.9% by weight, preferably less than 0.7% by weight based on the weight of the mixture.

In another aspect of the present invention the mixture provided in (i) is a mixture comprising a solvent and a non-sodium compound of avibactam, e.g. avibactam tetrabutylammonium or avibactam free acid. In this case, and also for other non-sodium salts of avibactam, it is necessary to add a suitable sodium source to the mixture in step (i) and/or (ii), preferably in step (ii). In a preferred embodiment, the sodium source is added to the mixture in step (ii) when the mixture has reached the increased temperature of at least 55° C., preferably of at least 70° C. and the positive pressure. Addition of the sodium source should not increase the water concentration of the mixture above 2% by weight, preferably not above 1.5% by weight, more preferably not above 1.3% by weight, even more preferably not above 0.7% by weight based on the weight of the mixture. Addition of the sodium salt can be carried out by addition in a single portion or by addition in smaller portions, e.g., dropwise over a predefined period of time, preferably in the range of from 2 min to 40 min, e.g., over a period of about 5 min, 10 min, 15 min, 20 min, or 30 min. After the sodium source has been completely added, it is preferred to maintain the increased temperature and positive pressure for at least about 5 min, e.g., about 5-40 min.

As regards the sodium source, said sodium source preferably comprises one or more alkaline sodium salt(s). In a preferred embodiment, the alkaline sodium salt is sodium 2-ethylhexanoate. In an even more preferred embodiment the sodium source is a solution of 2-ethylhexanoate in THF. In a preferred embodiment the molar ratio of the free acid of avibactam or of the salt of avibactam as defined hereinbefore, preferably of the tetrabutylammonium salt, to the sodium source is in the range of from 1:0.9 to 1:3, preferably of from 1:1 to 1:2, more preferably wherein the molar ratio is about 1:2. In another preferred embodiment the weight ratio of the free acid of avibactam or of the salt of avibactam as defined hereinbefore, preferably of the tetrabutylammonium salt, to the sodium source is in the range of from 1:0.9 to 1:3, preferably of from 1:1 to 1:2, more preferably wherein the weight ratio is about 1:2.

In a preferred embodiment of this aspect, the avibactam or salt thereof provided in (i) is a salt of avibactam, wherein the anion is a compound of formula (X),

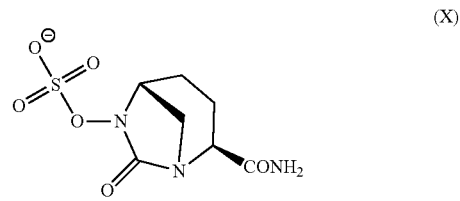 [SMILES: NC(=O)[C@@H]1CC[C@@H]2CN1C(=O)N2OS(=O)(=O)[O-]]

(X)

and the cation is M⁺, wherein M⁺ is N⁺RR'R"R''', and wherein R, R', R" and R''' are each independently selected from hydrogen and an alkyl group having 1 to 6 carbon atoms. Preferably, the cation W is tetrabutylammonium.

In an especially preferred embodiment of this aspect of the invention, the mixture provided in (i) is a solution comprising avibactam tetrabutylammonium and a solvent, or a suspension comprising avibactam free acid and a solvent. In this embodiment, it is preferred to add the sodium source, e.g. a solution of sodium 2-ethylhexanoate, to the mixture in step (ii), preferably when the mixture has reached the increased temperature of at least 55° C., preferably of at least 70° C. It is also preferred to add the sodium source dropwise, preferably over a period of about 2 min to 30 min, preferably over a period of about 5 min to 10 min, and to maintain the increased temperature and positive pressure in (ii) for a total of about 10-50 min. It is also preferred that addition of the sodium source does not increase the water content of the mixture above 2.0% by weight, more preferred not above 1.5% by weight, still more preferred not above 1.3% by weight, even more preferred not above 0.7% by weight based on the weight of the mixture. For example, the water content of the sodium source and of the solvent of the mixture provided in (i) can be chosen accordingly.

In another preferred embodiment of this aspect, the avibactam or salt thereof provided in (i) is avibactam free acid. Preferably, the free acid of avibactam is in crystalline form characterized by having a PXRD comprising reflections at 2-Theta angles of (9.6±0.2)°, (11.1±0.2)° and (17.4±0.2)°, when measured with CuKalpha$_{1,2}$ radiation having a wavelength of 0.15419 nm.

In certain cases of the above aspects of the invention, it may be useful, e.g. for the purpose of improving the purity and the yield of avibactam form C, to include in (i) a pre-treatment step of the avibactam or salt thereof with the same type of solvent as generally used in (i) but having a water content of at least 2% by weight, before reducing the water content of the mixture to a value of less than 2% by weight based on the total weight of the mixture, or to any lower value as defined hereinabove.

Thus, in one embodiment step (i) is
providing a mixture, preferably a suspension, comprising
avibactam sodium in crystalline form "B" and/or "D"

and a solvent having a water content of at least 2% by weight, preferably greater than 5% by weight, incubating the mixture, preferably for at least 6 h, more preferably at least 8 h, still more preferably at least 12 h, most preferably at least 20 h, and subsequently reducing the water content of the mixture to less than 0.9% by weight, preferably less than 0.7% by weight based on the weight of the mixture.

In another embodiment step (i) is providing a mixture, preferably a suspension, comprising free acid of avibactam and a solvent having a water content of at least 2% by weight, preferably greater than 5% by weight, adding a suitable sodium source, optionally incubating the mixture, and subsequently reducing the water content of the mixture to less than 0.9% by weight, preferably less than 0.7% by weight, based on the weight of the mixture.

Also in this embodiment, the pre-treatment disclosed in the previous embodiment is included. However, the starting material in this case being free acid of avibactam, it is necessary to include the addition of a suitable sodium source. The incubation step before reducing the water content of the mixture is optional in this instance. If included, incubation may be as short as 0.5 min, 1 min or 2 min. For example, incubation may be for 5 min, for 12 h or for 24 h.

In another embodiment step (i) is providing a mixture, preferably a solution, comprising a salt of avibactam, wherein the anion is a compound of formula (X),

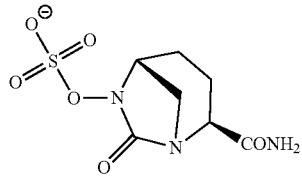

(X)

and the cation is M⁺, wherein W is N⁺RR'R"R"', and wherein R, R', R" and R"' are each independently selected from hydrogen and an alkyl group having 1 to 6 carbon atoms, and a solvent having a water content of at least 2% by weight, preferably greater than 5% by weight, adding a suitable sodium source, optionally incubating the mixture, and subsequently reducing the water content of the mixture to less than 0.9% by weight, preferably less than 0.7% by weight, based on the weight of the mixture.

Also in this embodiment, the pre-treatment disclosed in previous embodiments is included.

The starting material in this case being a non-sodium salt of avibactam, it is necessary to include the addition of a suitable sodium source. Preferably, the cation M⁺ is tetrabutylammonium. The incubation step before reducing the water content is optional in this instance. If included, incubation may be as short as 0.5 min, 1 min or 2 min. For example, incubation may be for 5 min, for 12 h or for 24 h.

The following explanations pertaining to the pre-treatment step and/or the reduction of the water content of the mixture equally apply to any of the corresponding embodiments recited hereinabove which include one or more of these features.

As regards the pre-treatment step of the avibactam or salt thereof with the same type of solvent as generally used in (i) but having a water content of at least 2% by weight (e.g. greater than 5% by weight), it is preferred that the solvent having a water content of at least 2% by weight has a water content in the range of from 2% by weight to 12% by weight, more preferably of from 3% by weight to 10% by weight, still more preferably of from 5% by weight to 8% by weight. Preferably, said pre-treatment step of the avibactam or salt thereof with the same type of solvent as generally used in (i) but having a water content of at least 2% by weight is carried out at about room temperature. As used herein the expression "the same type of solvent" means that the solvents are the same chemical compound and differ only in their respective water content.

As regards the reduction of the water content of the mixture, the water content may be reduced using any of the methods known to those skilled in the art such as addition of solvent having a suitably reduced water content, membrane techniques such as reverse osmosis, chemisorption or adsorption on desiccants such as molecular sieves. Preferably, it is reduced by adding a solvent having a suitably reduced water content, preferably by adding a solvent having a water content below 0.2% by weight, more preferably below 0.1% by weight, most preferably by adding dry solvent. Preferably, the solvent having a suitably reduced water content is also the same type of solvent as generally used in (i), similarly as for the solvent having a water content of at least 2% by weight. The solvent having a suitably reduced water content is added in an amount sufficient to provide in step (ii) a final water content of the mixture of less than 2% by weight, preferably less than 0.9% by weight, more preferably less than 0.7% by weight based on the total weight of the mixture.

Alternatively to this method of reducing the water content of the mixture by dilution, any other useful method may be used. For example, a precipitate formed during incubation with a solvent having a water content of at least 2% by weight may be separated from the mixture and resuspended in a solvent having a water content of less than 2% by weight, preferably less than 0.9% by weight, more preferably less than 0.7% by weight based on the weight of the resuspending solvent.

In general, it is preferred that the concentration of the avibactam or salt thereof in the mixture provided in (i) is in the range of from 3 g/L to 50 g/L, preferably of from 5 g/L to 30 g/L. In preferred embodiments, the concentration is about 10 g/L, 15 g/L, or 30 g/L.

In a highly preferred embodiment, the process of the present invention produces crystalline form C of avibactam sodium, which is polymorphically pure or essentially polymorphically pure, i.e. which is free or essentially free of any other physical forms, in particular free or essentially free of forms A, B, D and E of avibactam sodium as described in WO 2011/042560 A1.

As is apparent from the description of the process of the present invention hereinabove, avibactam sodium in polymorphic form C is preferably obtained in the form of a suspension in the solvent. Therefore, the process of the present invention may also comprise further steps, carried out subsequently to step (ii). In a preferred embodiment, the process comprises a further step (iii) cooling the mixture obtained in step (ii).

Preferably, the mixture is cooled to a temperature below 25° C., preferably to a temperature in the range of 10–20° C.

Following step (ii) or (iii), the process may also comprise a further step (iv) isolating the polymorphic form C of avibactam from the mixture obtained in (ii) or (iii).

Preferably, isolating in (iv) comprises filtering. In a specific embodiment, filtering comprises filtering under a gaseous atmosphere having a relative humidity of below 63%. Filtering may comprise using a pressure frit/strainer.

Additionally, isolating in (iv) may further comprise drying after filtering, e.g. in a vacuum drying oven.

Generally, one or more steps of the process of the invention may be carried out under agitation. Preferably one or more of step (i), step (ii), the pre-treatment step, reducing the water content, addition of a sodium source, and/or maintaining the mixture at the increased temperature and positive pressure may be carried out under agitation.

The present invention also relates to crystalline form C of avibactam sodium obtained according to the process of the present invention, which is preferably polymorphically pure or essentially polymorphically pure. The present invention further relates to a pharmaceutical composition comprising crystalline form C of avibactam sodium obtained according to the process of the present invention and the use of same in medicine and/or in a method of treatment as detailed in PCT/EP2016/068925.

Definitions

Unless indicated otherwise the terms used herein have the following meanings:

As used herein the term "avibactam" refers to [(2S,5R)-2-carbamoyl-7-oxo-1,6-diazabicylco[3.2.1]octan-6-yl] hydrogen sulfate which can be represented by the chemical structure according to Formula (I) herein, or a salt thereof.

As used herein the term "room temperature" refers to a temperature in the range of from 15 to 35° C., preferably of from 20 to 30° C., e.g. a temperature of about 25° C.

The term "reflection" with regards to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately $10^3$ to $10^{20}$ atoms, whereas short-range order is over a few atoms only (see *"Fundamentals of Powder Diffraction and Structural Characterization of Materials"* by Vitalij K. Pecharsky and Peter Y. Zayalij, Kluwer Academic Publishers, 2003, page 3).

As used herein, the term "essentially polymorphically pure" with reference to crystalline form C of avibactam sodium means that the form of avibactam so produced includes less than about 20%, preferably less than about 10%, more preferably less than about 5%, even more preferably less than about 3% and most preferably less than about 1% by weight, based on the weight of avibactam, of any other physical form of avibactam sodium.

The term "physical form" as used herein refers to any crystalline or amorphous phase of a material.

The term "form C" or "crystalline form C" as used herein refers to the crystalline form of avibactam sodium disclosed in PCT/EP2016/068925. Form C may be characterized by analytical methods well known in the field of the pharmaceutical industry for characterizing solids. Such methods comprise but are not limited to powder X-ray diffraction (PXRD), Fourier transform infrared (FTIR) spectroscopy, differential scanning calorimetry (DSC), thermogravimetric analysis (TGA) and gravimetric moisture sorption (GMS). Form C may be characterized by one of the aforementioned methods or by combining two or more of them. Crystalline form C of avibactam sodium is characterized by having a powder X-ray diffractogram comprising reflections at 2-Theta angles of (6.5±0.2)°, (14.4±0.2)°, (15.5±0.2)°, (18.0±0.2)° and (19.3±0.2)°, when measured at room temperature with Cu-Kalpha$_{1,2}$ radiation having a wavelength of 0.15419 nm. Alternatively or additionally, crystalline form C of avibactam sodium is characterized by having a Fourier transform infrared spectrum comprising peaks at wavenumbers of (3459±2) cm$^{-1}$, (1690±2) cm$^{-1}$, (1287±2) cm$^{-1}$, (1247±2) cm$^{-1}$ and (690±2) cm$^{-1}$, when measured at room temperature with a diamond ATR cell.

The term "form A" or "crystalline form A" as used herein refers to the crystalline monohydrate of avibactam sodium disclosed in WO 2011/042560 A1 which is characterized by having a PXRD comprising reflections at 2-Theta angles of (8.5±0.2)°, (15.3±0.2)° and (16.4±0.2)°, when measured with Cu-Kalpha$_{1,2}$ radiation having a wavelength of 0.15419 nm.

The term "form B" or "crystalline form B" as used herein refers to the crystalline form of avibactam sodium disclosed in WO 2011/042560 A1 which is characterized by having a PXRD comprising reflections at 2-Theta angles of (13.0±0.2)°, (16.5±0.2)°, (17.2±0.2)°, when measured with Cu-Kalpha$_{1,2}$ radiation having a wavelength of 0.15419 nm.

The term "form D" or "crystalline form D" as used herein refers to the crystalline form of avibactam sodium disclosed in WO 2011/042560 A1 which is characterized by having a PXRD comprising reflections at 2-Theta angles of (16.2±0.2)°, (17.4±0.2)°, (17.8±0.2)°, when measured with Cu-Kalpha$_{1,2}$ radiation having a wavelength of 0.15419 nm.

The term "form E" or "crystalline form E" as used herein refers to the crystalline form of avibactam sodium disclosed in WO 2011/042560 A1 which is characterized by having a PXRD comprising reflections at 2-Theta angles of (13.7±0.2)°, (15.0±0.2)° and (15.4±0.2)°, when measured with Cu-Kalpha$_{1,2}$ radiation having a wavelength of 0.15419 nm.

The "crystalline free acid of avibactam" as used herein is characterized by having a PXRD comprising reflections at 2-Theta angles of (9.6±0.2)°, (11.1±0.2)° and (17.4±0.2)°, when measured with CuKalpha$_{1,2}$ radiation having a wavelength of 0.15419 nm The term "about" as used herein means within 5%, more typically within 1% and most typically within 0.5% of the indicated value or range.

As used herein the term "isolated" with reference to avibactam corresponds to avibactam that is physically separated from the reaction mixture in which it is formed.

The term "agitation" as used herein relates to any motion of a macroscopic constituent of a solution or suspension which is induced from outside, relative to another macroscopic constituent of the solution or suspension. The term "mechanical agitation" as used herein relates to any motion of a macroscopic constituent of a solution or suspension which is induced from outside via a device, such as shaking or stirring or sonication, relative to another macroscopic constituent of the solution. The term "stirring" as used herein relates to any motion of a macroscopic constituent of a solution or suspension which is induced from outside via a stirring device, relative to another macroscopic constituent of the solution or suspension.

As used herein, the terms "water content" and "water concentration" are used interchangeably and refer to the quantity of water contained in a material, e.g. in a solvent or mixture such as a suspension or a solution. The water content can be determined by any method known in the art, e.g. by Karl Fischer (KF) titration. Typically, the water content is defined as % weight by total weight.

As used herein, the term "suspension" comprises mixtures comprising a solid and a liquid phase. However, at least a portion of the total amount of the compound representing the solid phase may be present in dissolved form in the liquid phase. For example, about 1%, 10%, 30% or 50% by weight, based on the total weight of the compound forming the solid phase may be dissolved in the liquid phase.

The present invention is further illustrated by the following embodiments and combinations of embodiments as indicated by the respective dependencies and references.

1. A process for the preparation of avibactam sodium in polymorphic form C having a powder X-ray diffractogram comprising reflections at 2-Theta angles of (6.5±0.2)°, (14.4±0.2)°, (15.5±0.2)°, (18.0±0.2)° and (19.3±0.2)°, when measured at a temperature in the range of from 20 to 30° C. with Cu-Kalpha$_{1,2}$ radiation having a wavelength of 0.15419 nm, comprising the steps
   (i) providing a mixture comprising avibactam or a salt thereof and a solvent, wherein the mixture has a water content of less than 2% by weight based on the weight of the mixture,
   (ii) increasing the temperature of the mixture provided in (i) to at least 55° C. and providing a positive pressure, adding a sodium source to the mixture in step (i) and/or (ii) if the form of avibactam provided in (i) is not avibactam sodium,
   thereby obtaining avibactam sodium in polymorphic form C.

2. The process according to embodiment 1, wherein (ii) is conducted in a sealed reaction vessel.

3. The process according to any of the preceding embodiments, wherein the mixture in (i) has a water content of less than 1.5% by weight, preferably less than 1.3% by weight, more preferably less than 0.7% by weight, most preferably less than 0.6% by weight based on the weight of the mixture.

4. The process according to any of the preceding embodiments, wherein the solvent is selected from the group consisting of alcohols, esters, ethers, ketones, carbonates, each having an alkyl chain of at least 4 carbon atoms, and mixtures thereof.

5. The process according to any of the preceding embodiments, wherein the solvent has 4-10 carbon atoms, preferably 4-8 carbon atoms, more preferably 4-6 carbon atoms.

6. The process according to any of the preceding embodiments, wherein the solvent is selected from the group consisting of a $C_4$-$C_6$ alcohol, a $C_4$-$C_6$ ester, a $C_4$-$C_6$ cyclic ether, a linear or cyclic ketone, a carbonate, and mixtures thereof.

7. The process according to any of the preceding embodiments, wherein the solvent is selected from the group consisting of isobutanol, n-butanol, 2-butanol, 2-methyl-2-butanol, 1,4-dioxane, THF, methyl-THF, ethyl acetate, isobutyl acetate, cyclohexanone, methyl ethyl ketone, methyl isobutyl ketone, diethyl carbonate.

8. The process according to any of the preceding embodiments, wherein the solvent is selected from the group consisting of isobutanol, n-butanol, 2-butanol, 2-methyl-2-butanol, 1,4-dioxane, methyl isobutyl ketone, ethyl acetate.

9. The process according to any of the preceding embodiments, wherein the positive pressure in (ii) is a positive pressure of at least 5 mbar, preferably at least 8 mbar, more preferably at least 10 mbar, still more preferably at least 15 mbar, still more preferably at least 20 mbar.

10. The process according to any of the preceding embodiments, wherein the positive pressure is generated by pressurization using an inert gas, the vapor pressure of the solvent used, or a mixture thereof.

11. The process according to any of the preceding embodiments, wherein the absolute pressure in (ii) is not more than 210 bar, preferably not more than 12 bar, more preferably not more than 8 bar, still more preferably not more than 5 bar.

12. The process according to any of embodiments 2-11, wherein an inert gas is added to the sealed reaction vessel in (ii).

13. The process according to the preceding embodiment, wherein the inert gas is selected from the group consisting of nitrogen and noble gases.

14. The process according to any of embodiments 12 to 13, wherein the inert gas is in a sufficient amount to provide a positive pressure in the sealed reaction vessel.

15. The process according to any of the preceding embodiments, wherein in (ii) the temperature is continuously increased.

16. The process according to any of the preceding embodiments, wherein in (ii) the temperature is increased to at least 59° C., preferably at least 63° C., more preferably at least 66° C., still more preferably at least 70° C., most preferably at least 73° C.

17. The process according to any of the preceding embodiments, wherein in (ii) the temperature is not higher than the decomposition temperature of the solvent.

18. The process according to any of the preceding embodiments, wherein in (ii) the temperature is increased to a temperature in the range of from 55° C. to 180° C., preferably of from 59° C. to 150° C., more preferably of from 63° C. to 140° C., still more preferably of from 66° C. to 135° C., still more preferably of from 70° C. to 130° C., most preferably of from 73° C. to 126° C.

19. The process according to any of the preceding embodiments, wherein in (ii) the temperature is increased to at least 66° C. and the positive pressure is a positive pressure of at least 5 mbar, preferably wherein in (ii) the temperature is increased to at least 70° C. and the positive pressure is a positive pressure of at least 5 mbar.

20. The process according to any of the preceding embodiments, wherein the increased temperature and positive pressure in (ii) is maintained for at least 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, or 20 minutes.

21. The process according to any of the preceding embodiments, wherein the increased temperature and positive pressure in (ii) is maintained for not more than 180 min, preferably not more than 120 min, more preferably not more than 60 min, still more preferably not more than 50 min, still more preferably not more than 45 min, most preferably not more than 40 min.

22. The process according to any of the preceding embodiments, wherein the increased temperature and positive pressure in (ii) is maintained for 2-50 min, preferably 5-45 min, more preferably 10-40 min, still more preferably 15-40 min, most preferably 20-40 min.

23. The process according to any of the preceding embodiments, wherein the mixture provided in (i) comprises avibactam or a salt thereof in crystalline form, amorphous form or a mixture thereof, preferably in crystalline form.

24. The process according to the preceding embodiment, wherein the avibactam or salt thereof provided in (i) is avibactam sodium.

25. The process according to any of the preceding embodiments, wherein the mixture provided in (i) is a mixture comprising a solvent and avibactam sodium in crystalline form "A" having a PXRD comprising reflections at 2-Theta angles of (8.5±0.2)°, (16.4±0.2)°, (17.1±0.2)°, crystalline form "B" having a PXRD comprising reflections at 2-Theta angles of (13.0±0.2)°, (16.5±0.2)°, (17.2±0.2)°, crystalline form "D" having a PXRD comprising reflections at 2-Theta angles of (16.2±0.2)°, (17.4±0.2)°, (17.8±0.2)°, or crystalline form "E" having a PXRD comprising reflections at 2-Theta angles of (13.7±0.2)°, (15.0±0.2)° and (15.4±0.2)° when measured at room temperature with CuKalpha$_{1,2}$ radiation having a wavelength of 0.15419 nm, or a mixture thereof, preferably in crystalline form "A".

26. The process according to any one of embodiments 1 to 23, wherein the avibactam or salt thereof provided in (i) is a salt of avibactam, wherein the anion is a compound of formula (X), (X)

and the cation is M$^+$, wherein W is 1\1+RR'R''R''', and wherein R, R', R'' and R''' are each independently selected from hydrogen and an alkyl group having 1 to 6 carbon atoms.

27. The process according to the preceding embodiment, wherein the sodium source is added to the mixture in step (ii).

28. The process according to any of embodiments 26 to 27, wherein the sodium source is added to the mixture in step (ii) when the mixture has reached an increased temperature of at least 55° C., preferably of at least 70° C.

29. The process according to any of embodiments 26 to 28, wherein the sodium source is added dropwise.

30. The process according to any of embodiments 26 to 29, wherein the sodium source is added over a period of about 2 min to 30 min, preferably over a period of about 5 min to 10 min, and wherein the increased temperature and positive pressure in (ii) is maintained for a total of about 10-50 min.

31. The process according to any of embodiments 1 to 25, wherein step (i) is providing a mixture comprising avibactam sodium in crystalline form "B" and/or "D" and a solvent having a water content of at least 2% by weight, preferably greater than 5% by weight, incubating the mixture, and subsequently reducing the water content of the mixture to less than 0.9% by weight, preferably less than 0.7% by weight, based on the weight of the mixture.

32. The process according to any one of embodiments 1 to 23, wherein step (i) is providing a mixture comprising free acid of avibactam and a solvent having a water content of at least 2% by weight, preferably greater than 5% by weight, adding a suitable sodium source, optionally incubating the mixture, and subsequently reducing the water content of the mixture to less than 0.9% by weight, preferably less than 0.7% by weight, based on the weight of the mixture.

33. The process according to the preceding embodiment, wherein the free acid of avibactam is in crystalline form characterized by having a PXRD comprising reflections at 2-Theta angles of (9.6±0.2)°, (11.1±0.2)° and (17.4±0.2)°, when measured with CuKalpha$_{1,2}$ radiation having a wavelength of 0.15419 nm.

34. The process according to any one of embodiments 1 to 23, wherein step (i) is providing a mixture comprising a salt of avibactam, wherein the anion is a compound of formula (X), (X)

and the cation is M$^+$, wherein M$^+$ is N$^+$RR'R''R''', and wherein R, R', R'' and R''' are each independently selected from hydrogen and an alkyl group having 1 to 6 carbon atoms, and a solvent having a water content of at least 2% by weight, preferably greater than 5% by weight, adding a suitable sodium source, optionally incubating the mixture, and subsequently reducing the water content of the mixture to less than 0.9% by weight, preferably less than 0.7% by weight, based on the weight of the mixture.

35. The process according to any of embodiments 26 to 30 or 34, wherein the cation M$^+$ is tetrabutylammonium.

36. The process according to any of embodiments 31 to 35, wherein the solvent having a water content of at least 2% by weight is as defined in any one of embodiments 4-8.

37. The process according to any one of embodiment 31 to 36, wherein the water content of the mixture is reduced by adding solvent having a suitably reduced water content, preferably by adding solvent having a water content below 0.2% by weight, more preferably below 0.1% by weight, most preferably by adding dry solvent.

38. The process according to any of the preceding embodiments, wherein the sodium source comprises one or more alkaline sodium salt(s).

39. The process according to the preceding embodiment, wherein the one or more alkaline sodium salt(s) is sodium 2-ethylhexanoate, preferably wherein the sodium source is a solution of sodium 2-ethylhexanoate.

40. The process according to any of the preceding embodiments, wherein the molar ratio of the free acid of avibactam or of the salt of avibactam to the sodium source is in the range of from 1:0.9 to 1:3, preferably of from 1:1 to 1:2, more preferably wherein the molar ratio is about 1:2.

41. The process according to any of the preceding embodiments, wherein the concentration of the avibactam or salt thereof in the mixture provided in (i) is in the range of from 3 g/L to 50 g/L, preferably of from 5 g/L to 30 g/L.

42. The process according to any one of the preceding embodiments, further comprising a step
(iii) cooling the mixture obtained in step (ii).

43. The process according to the preceding embodiment, wherein the mixture is cooled to a temperature below 25° C., preferably to a temperature in the range of 10–20° C.

44. The process according to any of the preceding embodiments, further comprising after step (ii) or (iii) a step isolating the polymorphic form C of avibactam from the mixture obtained in (ii)

45. The process according to the preceding embodiment, wherein isolating in (iv) comprises filtering.

46. The process according to the preceding embodiment, wherein filtering comprises filtering under a gaseous atmosphere having a relative humidity of below 63%.

47. The process according to any of embodiments 45 to 46, wherein filtering comprises using a pressure frit/strainer.

48. The process according to any of embodiments 45 to 47, wherein isolating in (iv) further comprises drying after filtering, e.g. in a vacuum drying oven.

The following examples illustrate the present invention and are not intended to limit the scope of the invention set forth in the claims appended hereto.

EXAMPLES

Example 1: Procedure for the Synthesis of Avibactam Sodium (AVIB.Na)—Polymorph C

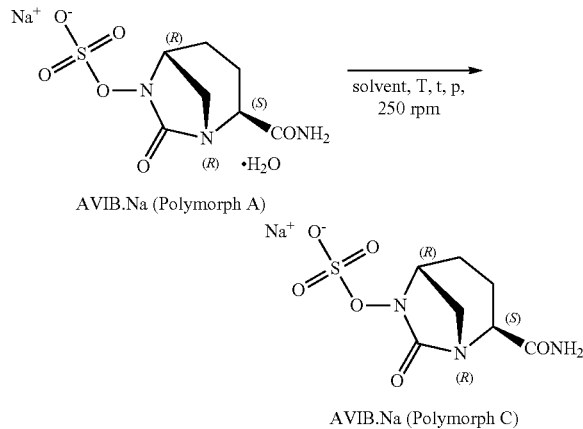

In table 1, various tested conditions for the transformation of AVIB.Na form A to form C are listed. Under all conditions, essentially pure AVIB.Na form C was obtained.

The following procedure describes in detail the reaction as listed in entry 1:

In an autoclave, equipped with a magnetic stirrer, the monohydrate of AVIB.Na (Polymorph A, 100 mg, 0.33 mmol) was suspended in dry iBuOH (10 mL, 10 g/L). The autoclave was sealed, placed in an EasyMax reactor (Mettler Toledo: EasyMax 102 Advanced Synthesis Workstation) and the mixture was heated for 30 min (external heating (Tj)= 130° C.; maximum inner reaction temperature (Tr)=126° C., maximum overpressure: 1.0 bar). The suspension was then rapidly cooled down to room temperature and the white solid was collected via filtration, washed with small amounts of dry iBuOH and dried under high vacuum to yield 73% pure AVIB.Na—polymorph C. The formation of form C is confirmed by having a powder X-ray diffraction (PXRD) comprising reflections at 2-Theta angles of (6.5±0.2)°, (14.4±0.2)°, (15.5±0.2)°, (18.0±0.2)° and (19.3±0.2)° when measured at a temperature in the range of from 20 to 30° C. with Cu-Kalpha$_{1,2}$ radiation having a wavelength of 0.15419 nm.

TABLE 1

Various conditions for the formation of polymorphic form C of AVIB.Na:

| Entry | Temperature Tj/Tr (° C.) | Overpressure (bar) | Conc. (g/L) | Time (min) | Solvent (water concentration) | Yield |
|---|---|---|---|---|---|---|
| 1 | 130/126 | 1.0 | 10 | 30 | iBuOH (0.02 wt % H$_2$O) | 73% |
| 2 | 78/75 | 6.0$^a$ | 10 | 30 | iBuOH (0.02 wt % H$_2$O) | 77% |
| 3 | 130/126 | 1.0 | 10 | 5 | iBuOH (0.02 wt % H$_2$O) | —$^b$ |
| 4 | 130/126 | 10.0$^a$ | 30 | 5 | iBuOH (0.02 wt % H$_2$O) | —$^b$ |
| 5 | 78/75 | 6.0$^a$ | 15 | 18 | iBuOH (0.51 wt % H$_2$O) | —$^b$ |
| 6 | 78/75 | 6.0$^a$ | 15 | 30 | nBuOH (0.07 wt % H$_2$O) | —$^b$ |
| 7 | 78/75 | 6.0$^a$ | 15 | 30 | 2-BuOH (0.05 wt % H$_2$O) | —$^b$ |
| 8 | 78/75 | 6.0$^a$ | 15 | 30 | 2-Me-2-BuOH (0.06 wt % H$_2$O) | —$^b$ |
| 19 | 78/75 | 6.0$^a$ | 15 | 30 | EtOAc (0.06 wt % H$_2$O) | —$^b$ |
| 10 | 78/75 | 6.0$^a$ | 15 | 30 | MIBK (0.07 wt % H$_2$O) | —$^b$ |
| 11 | 78/75 | 6.0$^a$ | 15 | 30 | MEK (0.11 wt % H$_2$O) | —$^b$ |
| 12 | 78/75 | 6.0$^a$ | 15 | 30 | Cyclohexanone (0.11 wt % H$_2$O) | —$^b$ |
| 13 | 78/75 | 6.0$^a$ | 15 | 30 | 1,4-Dioxane (0.15 wt % H$_2$O) | —$^b$ |

$^a$the overpressure was generated with N$_2$-gas;
$^b$the yield was not determined Example 2: Autoclave—Free Procedure for the Synthesis of AVIB.Na—Polymorph C In a glass vessel, equipped with a magnetic stirrer and connected to a manometer, the monohydrate of AVIB.Na (Polymorph A, 100 mg, 0.33 mmol) was suspended in dry iBuOH (10 mL, 10 g/L). The vial was sealed, placed in an EasyMax reactor and the mixture was heated for 30 min (Tj=78° C.; maximum Tr=75° C.; an overpressure of 8 mbar was measured). The suspension was then rapidly cooled down to room temperature and the white solid was collected via filtration, washed with small amounts of dry iBuOH and dried under high vacuum to yield pure AVIB.Na—polymorph C. The formation of form C is confirmed by having a powder X-ray diffraction (PXRD) comprising reflections at 2-Theta angles of (6.5±0.2)°, (14.4±0.2)°, (15.5±0.2)°, (18.0±0.2)° and (19.3±0.2)°.

Example 3: Scale-Up Procedure for the Synthesis of AVIB.Na—Polymorph C

In an autoclave with a mechanical anchor stirrer, the monohydrate of AVIB.Na (Polymorph A; 36.3 g, 0.119 mol) was suspended in dry iBuOH (1.2 L, 30 g/L). The autoclave was sealed and the mixture was heated for 30 min under stirring (Tj=130° C.; maximum Tr=119° C., maximum overpressure: 0.5 bar). After cooling the reaction mixture to 20° C. within 45 min, the autoclave was opened and the white suspension was transferred into a pressure filter. The autoclave was rinsed with 200 mL dry iBuOH. Pure polymorphic form C of AVIB.Na (33.3 g) was obtained (Purity: 98.3%+ 0.5% iBuOH; Yield: 96%). The formation of form C is confirmed by having a PXRD comprising reflections at 2-Theta angles of (6.5±0.2)°, (14.4±0.2)°, (15.5±0.2)°, (18.0±0.2)° and (19.3±0.2)°.

Example 4: Preparation of AVIB.Na Polymorph C from Polymorph B/D

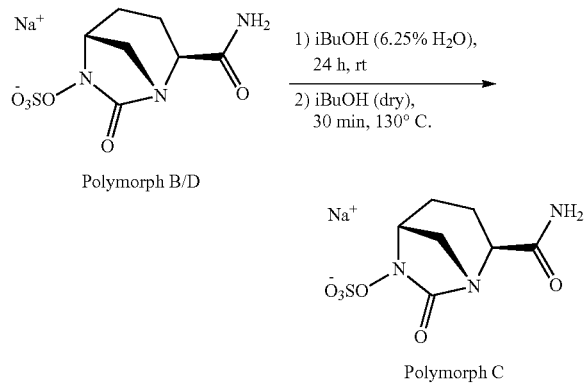

Polymorph B/D → Polymorph C

In an autoclave equipped with a magnetic stirrer, AVIB.Na (polymorphic form D, 200 mg, 0.70 mmol) was suspended in iBuOH (6.25 wt % H$_2$O, 2 mL, 100 g/L) and the reaction was stirred at room temperature for 24 h at atmospheric pressure. Then, dry iBuOH (20 mL) was added to the suspension and the water concentration was measured using a KF-coulometer (below 0.6 wt % H$_2$O). The autoclave was sealed and the reaction was heated under stirring for 30 min (Tj=130° C.; maximum Tr=126° C., maximum overpressure: 1.0 bar). The suspension was then rapidly cooled down to room temperature and the white solid was collected via filtration, washed with small amounts of dry iBuOH and dried under high vacuum to obtain AVIB.Na Polymorph C in 59% yield. The formation of form C is confirmed by having a PXRD comprising reflections at 2-Theta angles of (6.5±0.2)°, (14.4±0.2)°, (15.5±0.2)°, (18.0±0.2)° and (19.3±0.2)°.

Example 5: Preparation of AVIB.Na Polymorph C from AVIB.Free

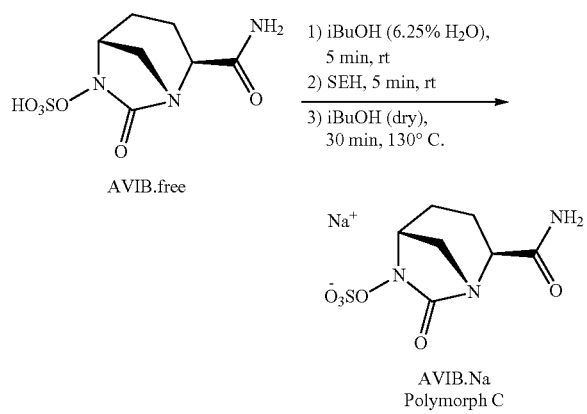

AVIB.free → AVIB.Na Polymorph C

An autoclave, equipped with a magnetic stirrer, was charged with avibactam free acid (AVIB.free (e.g. prepared according to the procedure disclosed in EP16185913.7); 200 mg, 0.75 mmol, 1.0 equiv) and iBuOH (6.25 wt % H$_2$O, 2 mL, 100 g/L), before a freshly prepared solution of sodium 2-ethylhexanoate (SEH, 1.0 mL, 1.7 mmol, 1.7 M, 2.3 equiv) was added dropwise to the reaction and the suspension was stirred at room temperature for 5 min at atmospheric pressure. Next, dry iBuOH (36 mL) was added and the water concentration was determined by a KF-coulometer (below 0.6 wt % H$_2$O). The autoclave was sealed and an overpressure of 5.5 bar was generated with N$_2$-gas. The reaction was heated under stirring for 30 min (Tj=78° C.; maximum Tr=75° C., maximum overpressure: 6.0 bar). The suspension was then rapidly cooled down to room temperature and the white solid was collected via filtration, washed with small amounts of dry iBuOH and dried under high vacuum to obtain AVIB.Na Polymorph C in 54% yield. The formation of form C is confirmed by having a PXRD comprising reflections at 2-Theta angles of (6.5±0.2)°, (14.4±0.2)°, (15.5±0.2)°, (18.0±0.2)° and (19.3±0.2)°.

Example 6: Preparation of AVIB.Na Polymorph C from AVIB.TBA

Option 1: Autoclave—Procedure:

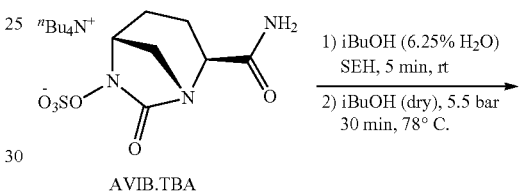

AVIB.TBA

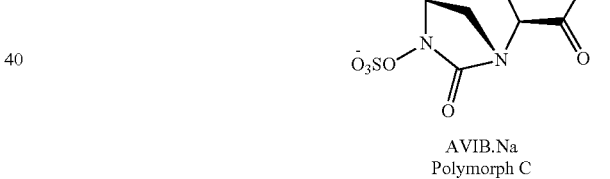

AVIB.Na Polymorph C

A 50 mL autoclave, equipped with a magnetic stirrer, was charged with avibactam tetrabutylammonium salt (AVIB.TBA; 400 mg, 0.79 mmol, 1.0 equiv) and iBuOH (6.25 wt % H$_2$O, 2 mL, 200 g/L), before a freshly prepared solution of SEH (1.0 mL, 1.7 mmol, 1.7 M, 2.1 equiv) was added dropwise to the solution and the resulting suspension was stirred at room temperature for 5 min at atmospheric pressure. Next, dry iBuOH (36 mL) was added and the water concentration was determined by a KF-coulometer (below 0.6 wt % H$_2$O). The autoclave was sealed and an overpressure of 5.5 bar was generated with N$_2$-gas. The reaction was heated under stirring for 30 min (Tj=78° C.; maximum Tr=75° C., maximum overpressure: 6.0 bar). The suspension was then rapidly cooled down to room temperature and the white solid was collected via filtration, washed with small amounts of dry iBuOH and dried under high vacuum to obtain AVIB.Na Polymorph C in 49% yield. The formation of form C is confirmed by having a PXRD comprising reflections at 2-Theta angles of (6.5±0.2)°, (14.4±0.2)°, (15.5±0.2)°, (18.0±0.2)° and (19.3±0.2)°.

Option 2: Autoclave—Free Procedure:

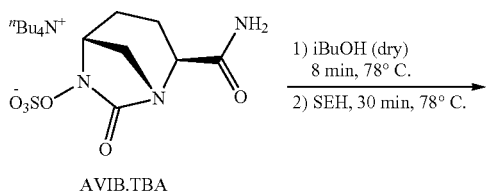

AVIB.TBA

AVIB.Na
Polymorph C

In a glass vessel, equipped with a magnetic stirrer, the tetrabutylammonium salt of Avibactam (AVIB.TBA, 394 mg, 0.78 mmol, 1.0 equiv)) was dissolved in dry iBuOH (10 mL, 40 g/L). The reaction vessel was sealed with a septum, placed in an EasyMax reactor and the mixture was heated to 78° C. (Tj) and stirred for 8 min before a freshly prepared solution of SEH (1.0 mL, 1.7 mmol, 1.7 M, 2.1 equiv) was added dropwise over 6 minutes through the septum (no pressure relief valve was connected). A white suspension was formed immediately and the mixture was held at this temperature for 30 min (Tj=78° C.; maximum Tr=75° C.) before it was rapidly cooled to room temperature. The white solid was collected via filtration, washed with small amounts of dry iBuOH and dried under high vacuum to obtain pure AVIB.Na—Polymorph C in 54% yield. The formation of form C is confirmed by having a PXRD comprising reflections at 2-Theta angles of (6.5±0.2)°, (14.4±0.2)°, (15.5±0.2)°, (18.0±0.2)° and (19.3±0.2)°.

Option 3: Scale-Up Reaction:

For this experiment, the sodium 2-ethylhexanoate solution was prepared from 44.3 mL 2-ethylhexanoic acid, 22.1 g NaOH and 100 mL THF.

In a 10 L Schmizo-reactor, equipped with a mechanical anchor stirrer, an inlet temperature sensor and a dropping funnel, AVIB.TBA (133.2 g, 262.8 mmol, 1.0 equiv) was dissolved in dry iBuOH (6.70 L, 99%) under stirring (180 rpm). The reactor was tightly sealed (septum), the dropping funnel was charged with the sodium 2-ethylhexanoate and sealed as well. The reaction was heated to 80° C. (=Tj) and stirring was continued for 45 min at this temperature (Tr=74° C.). Next, the solution of sodium 2-ethylhexanoate in THF was added dropwise over 30 min to the reaction mixture and stirring was continued for further 20 min. The resulting suspension was cooled down to 10° C. (=Tr; Tj=0° C.) over 1.75 h and the white solid was collected via filtration, washed with dry iBuOH (2×150 mL) and dried under vacuum to yield 38.2 g of pure AVIB.Na polymorph C (51%). The formation of form C is confirmed by having a PXRD comprising reflections at 2-Theta angles of (6.5±0.2)°, (14.4±0.2)°, (15.5±0.2)°, (18.0±0.2)° and (19.3±0.2)°.

Example 7: General Procedures

Preparation of the SEH-Solution (Unless Described Differently):

A 50 mL flask, equipped with a magnetic stirrer, was charged with NaOH (1.45 mL, 50 wt %, 27.6 mmol, 1.0 equiv) and THF (10 mL) and cooled to 0° C. 2-Ethylhexanoic acid (4.85 mL, 30.9 mmol, 1.1 equiv) was added dropwise to the mixture and the solution was allowed to warm up to room temperature and stirring was continued for 5 h.

PXRD:

Powder X-ray diffraction (PXRD) was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-Theta with 40 s per step (255 channels) in the angular range of 2° to 40° 2-Theta at ambient conditions. A typical precision of the 2-Theta values is in the range of ±0.2° 2-Theta. Thus, the diffraction peak of substantially pure form C that appears for example at 6.5° 2-Theta can appear between 6.3 and 6.7° 2-Theta on most X-ray diffractometers under standard conditions.

Water Content:

The water content was determined with a Metrohm 831 KF Coulometer equipped with a Metrohm 703 Ti Stand stirrer (speed: 4) and diaphragma. An extraction time of 60 seconds was adjusted when using Hydranal Coulomat AK reagent.

The invention claimed is:

1. A process for the preparation of avibactam sodium in polymorphic form C having a powder X-ray diffractogram comprising reflections at 2-Theta angles of (6.5±0.2)°, (14.4±0.2)°, (15.5±0.2)°, (18.0±0.2)° and (19.3±0.2)°, when measured at a temperature in the range of from 20 to 30° C. with Cu-Kalpha$_{1,2}$ radiation having a wavelength of 0.15419 nm, comprising the steps
  (i) providing a mixture comprising avibactam or a salt thereof and a solvent, wherein the mixture has a water content of less than 2% by weight based on the weight of the mixture,
  (ii) increasing the temperature of the mixture provided in (i) to at least 55° C. and increasing the pressure relative to step (i),
    adding a sodium source to the mixture in step (i) and/or (ii) if the form of avibactam provided in (i) is not avibactam sodium,
    thereby obtaining avibactam sodium in polymorphic form C.

2. The process according to claim 1, wherein the mixture in (i) has a water content of less than 1.5% by weight based on the weight of the mixture.

3. The process according to claim 1, wherein the solvent is selected from the group consisting of alcohols, esters, ethers, ketones, carbonates, each having an alkyl chain of at least 4 carbon atoms, and mixtures thereof.

4. The process according to claim 1, wherein the solvent is selected from the group consisting of a $C_4$-$C_6$ alcohol, a $C_4$-$C_6$ ester, a $C_4$-$C_6$ cyclic ether, a linear or cyclic ketone, a carbonate, and mixtures thereof.

5. The process according to claim 1, wherein the solvent is selected from the group consisting of isobutanol, n-butanol, 2-butanol, 2-methyl-2-butanol, 1,4-dioxane, THF, methyl-THF, ethyl acetate, isobutyl acetate, cyclohexanone, methyl ethyl ketone, methyl isobutyl ketone, and diethyl carbonate.

6. The process according to claim 1, wherein the pressure in (ii) is increased by at least 5 mbar.

7. The process according to claim 1, wherein in (ii) the temperature is increased to at least 59° C.

8. The process according to claim 1, wherein in (ii) the temperature is increased to a temperature in the range of from 55° C. to 180° C.

9. The process according to claim 1, wherein the mixture provided in (i) comprises avibactam or a salt thereof in crystalline form, amorphous form or a mixture thereof.

10. The process according to claim 1, wherein the mixture provided in (i) is a mixture comprising a solvent and avibactam sodium in crystalline form "A" having a PXRD comprising reflections at 2-Theta angles of (8.5±0.2)°, (16.4±0.2)°, (17.1±0.2)°, crystalline form "B" having a PXRD comprising reflections at 2-Theta angles of (13.0±0.2)°, (16.5±0.2)°, (17.2±0.2)°, crystalline form "D" having a PXRD comprising reflections at 2-Theta angles of (16.2±0.2)°, (17.4±0.2)°, (17.8±0.2)°, or crystalline form "E" having a PXRD comprising reflections at 2-Theta angles of (13.7±0.2)°, (15.0±0.2)° and (15.4±0.2)°, when measured at room temperature with Cu-Kalpha$_{1,2}$ radiation having a wavelength of 0.15419 nm, or a mixture thereof.

11. The process according to claim 1, wherein the avibactam or salt thereof provided in (i) is a salt of avibactam, wherein the anion is a compound of formula (X),

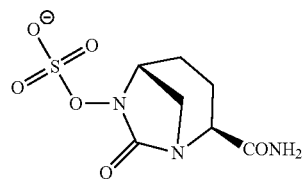

(X)

and the cation is M$^+$, wherein M$^+$ is N$^+$RR'R"R''', and where R, R', R" and R''' are each independently selected from hydrogen and an alkyl group having 1 to 6 carbon atoms.

12. The process according to claim 1, wherein step (i) is providing a mixture comprising avibactam sodium in crystalline form "B" and/or "D" and a solvent having a water content of at least 2% by weight,
incubating the mixture, and
subsequently reducing the water content of the mixture to less than 0.9% by weight, based on the weight of the mixture.

13. The process according to claim 1, wherein step (i) is providing a mixture comprising free acid of avibactam and a solvent having a water content of at least 2% by weight,
adding a suitable sodium source,
optionally incubating the mixture, and
subsequently reducing the water content of the mixture to less than 0.9% by weight, based on the weight of the mixture.

14. The process according to claim 1, wherein step (i) is providing a mixture comprising a salt of avibactam, wherein the anion is a compound of formula (X),

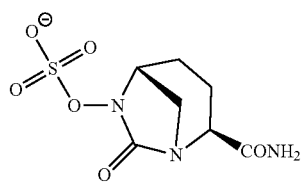

(X)

and the cation is M$^+$, wherein M$^+$ is N$^+$RR'R"R''', and wherein R, R', R" and R''' are each independently selected from hydrogen and an alkyl group having 1 to 6 carbon atoms, and a solvent having a water content of at least 2% by weight,
adding a suitable sodium source,
optionally incubating the mixture, and
subsequently reducing the water content of the mixture to less than 0.9% by weight, based on the weight of the mixture.

15. The process according to claim 1, wherein the sodium source comprises one or more alkaline sodium salt(s).

* * * * *